United States Patent
Li et al.

(10) Patent No.: US 8,128,945 B2
(45) Date of Patent: *Mar. 6, 2012

(54) DRUG DELIVERY SYSTEM TARGETING TO ESTROGEN RECEPTOR OVER-EXPRESSED CELLS

(75) Inventors: Shyh-Dar Li, Miaoli (TW); Ae-June Wang, Hsinchu (TW); Chung-Kung Lai, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/886,083

(22) Filed: Sep. 20, 2010

(65) Prior Publication Data

US 2011/0008262 A1    Jan. 13, 2011

Related U.S. Application Data

(63) Continuation of application No. 10/747,049, filed on Dec. 30, 2003, now Pat. No. 7,820,204.

(30) Foreign Application Priority Data

Dec. 31, 2002   (TW) ............................... 91138150 A

(51) Int. Cl.
*A61K 9/51* (2006.01)

(52) U.S. Cl. ........ 424/400; 977/773; 977/774; 564/324; 564/325

(58) Field of Classification Search ........................ None
See application file for complete search history.

(56) References Cited

U.S. PATENT DOCUMENTS

| | | |
|---|---|---|
| 5,219,548 A | 6/1993 | Yang et al. |
| 5,490,991 A | 2/1996 | Enriquez et al. |
| 6,056,973 A | 5/2000 | Allen et al. |
| 6,096,874 A | 8/2000 | Wallace et al. |
| 6,300,319 B1 | 10/2001 | Manoharan |
| 6,316,465 B1 | 11/2001 | Pershadsingh et al. |
| 6,350,431 B1 | 2/2002 | Snow et al. |
| 6,416,988 B1 | 7/2002 | Conklin et al. |
| 6,676,963 B1 | 1/2004 | Lanza et al. |
| 7,820,204 B2 * | 10/2010 | Li et al. ........................ 424/490 |

* cited by examiner

*Primary Examiner* — Brian J Davis

(74) *Attorney, Agent, or Firm* — Birch, Stewart, Kolasch & Birch, LLP

(57) ABSTRACT

A vector for targeted delivery of drugs into estrogen receptors over-expressed cells is disclosed. The vector of the present invention is mainly about an active targeting delivery carrier which consists of a plurality of nanoparticles including: (i) a plurality of targeted moiety conjugated to the outer surface of the nanoparticles, the moiety being capable of binding with the estrogen receptor of a target cell, and (ii) bioactive agents encapsulated in the nanoparticles or forming complex with the nanoparticles. The targeted moiety of the present invention can also be conjugated to parent drugs for prodrug design.

5 Claims, 4 Drawing Sheets

DRUG DELIVERY SYSTEM TARGETING TO ESTROGEN RECEPTOR OVER-EXPRESSED CELLS

REFERENCE TO RELATED APPLICATIONS

This is a Continuation of U.S. application Ser. No. 10/747,049, now U.S. Pat. No. 7,820,204, filed on Dec. 30, 2003, which claims priority for Application No. 091138150 filed in Taiwan R.O.C. on Dec. 31, 2002, the entire contents of which are hereby incorporated by reference and for which priority is claimed under 35 U.S.C. §120.

BACKGROUND OF THE INVENTION

1. Field of the Invention

The present invention relates to a drug delivery system, especially to a drug delivery system targeting estrogen receptor over-expressed cells.

2. Description of Related Art

Estrogen receptors (ER, herein after) are mainly expressed in ovarian, uterus and liver cells, and are found over-expressed in certain tumor cells, such as breast cancer, ovarian cancer, uterus cancer and prostate cancer. More and more studies since 1981 have revealed that the expression of ERs are high not only in nuclei but also on cell membranes for signal transduction.

Tamoxifen (Tam, herein after), an antiestrogen known to have high affinity for ERs, is a frequently used drug for treating and preventing breast cancer in clinical trials. Some researchers have synthesized a variety of Tam derivatives for imaging abnormal tissues with high ERs expression, such as breast cancer. However, except as a chemical therapeutic agent and imaging agent, there is no such application for Tam and its derivatives to serve as a ligand in drug delivery systems.

The conventional drugs, such as small molecule drugs, protein drugs, peptide drugs and nucleotides, or nanoparticle drug delivery systems, such as liposomes, polymers and emulsions, cannot specifically target to target-cells. Therefore, a specific ligand is needed for delivering the drugs or nanoparticle drug delivery systems to target cells with specific receptors, so as to increase the efficiency of the drugs and lower the side effects. Today, no targeted drugs are found on the market. Theoretically, it is possible to practice targeted delivery of drugs by employment of antigen/antibody conjugation, but the antigen/antibody may induce the immunogeneicity in the host, which may subsequently results in unpredictable consequences.

The term "targeted delivery system" is used to describe the system utilizing ligands that bind to the specific target receptors on target cells so as to guide the drugs or nanoparticles into the target cells. The examples of ligands include antibodies, antibody fragments, peptides or small molecule compounds that can be conjugated with drugs or attached to the surface of the nanoparticles. The receptors should be located on the surface of the target cells, and can trigger endocytosis after binding with the ligands. There are about 15 papers since 1981 to 2002 proving that ERs exist not only in the nuclei but also on the plasma membrane. V. D. Ramirez further proved that the binding of Tam with estrogen receptors could trigger endocytosis in HepG2 cells. This evidence implied the possibility of applying Tam as a targeted ligand for targeted delivery of drugs.

On the other hand, Tam is a frequently used drug for breast cancer treatment. However, there is no known application of Tam as a targeted ligand other than as a cancer-imaging agent.

To summarize, we hypothesize that Tam may be applicable as a targeted ligand, which can guide drugs or nanoparticle drug delivery systems to the surface of target cells and capable of inducing endocytosis so as to deliver certain specific matters into target cells.

SUMMARY OF THE INVENTION

It is the object of the present invention to provide a drug delivery system containing small molecule ligands on the surface capable of binding with the estrogen receptors (ERs) on the target cell membrane so as to specifically deliver drugs into the target cells by triggering endocytosis.

Another object of the present invention is to present a compound of formula (II):

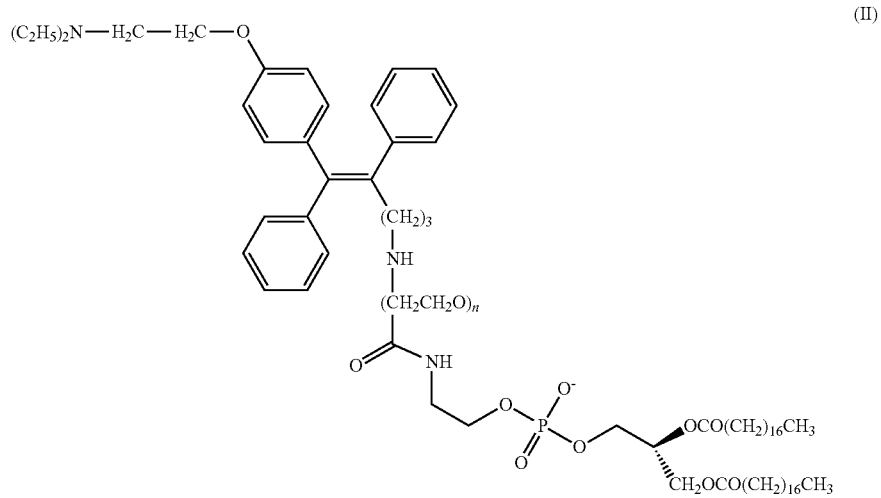

for inserting into nanoparticles to help the nanoparticles to target and bind with the estrogen receptors (ERs) on the target cell membrane for specific drug delivery.

To achieve the object, the drug delivery system for targeting estrogen receptor over-expressed cells of the present invention includes: a plurality of nanoparticles consisting of lipids, surfactants, charged peptides/proteins, and/or polymers; active ingredients being encapsulated in or formed complex with said nanoparticles; and a plurality of ligand derivatives being able to bind with estrogen receptors on the surface of target cells.

The present invention also provides a method for preparing the drug delivery system capable of specifically delivering drugs into estrogen receptor over-expressed cells.

The targeted drug delivery system is consisting of a plurality of nanoparticles which are comprised of lipids, surfactants, charged peptides/proteins, and/or polymers; active ingredients being encapsulated in or formed complex with said nanoparticles; and a plurality of ligand derivatives being able to bind with estrogen receptors on the surface of target cells. Surfactant here can be any conventional PEG derivatives for surfactant. Preferably, the PEG derivative of the surfactant is Span, Tween, Brij and so on. The charged peptides or proteins of the first surfactants here can be any conventional peptides or proteins. Preferably, the protein is protamine, histone, polyarginine, polyhistidine, polylysine and so on. The polymersphere can be any conventional polymer or polymer composition, which is capable of encapsulating drugs. Preferably, the polymer is PEI, chitosan, polylysine, or the combination thereof. The preparation for a nanoparticle can be any conventional method for preparing nanoparticles. Preferably, the nanoparticles is prepared by hydrating the mixtures of tamoxifen-PEG-DSPE (ligand derivatives capable of inserting into liposome lipid bilayer and presenting the ligands for targeting to estrogen receptor over-expressed cells), phosphocholine (PC), cholesterol (CHOL), and DSPE-PEG to obtain a liposome suspension, followed by mixing the liposome suspension with a solution having bioactive materials, charged peptides, proteins, or polymers, to obtain bioactive material containing nanoparticles.

Moreover, the drug delivery system of the present invention adopts Tam and Tam derivative for targeting or guiding the delivery system to the estrogen receptor over-expressed cells. The targeted nanoparticles inserted with the ligand derivatives having moiety of Tam can recognize or target the ER over-expressed cells. Furthermore, the targeted nanoparticles inserted with the ligand derivatives of the present invention can trigger receptor-mediated endocytosis and deliver drugs into the target cells. Tam derivative for the present invention can be any compound having a structure of the formula (I):

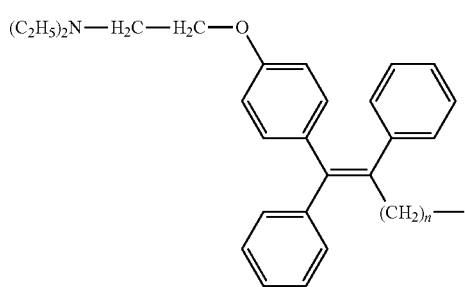

wherein n is an integer less than 10.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENT

Based on the ideas of the invention described above, Tam can be also applied for targeted prodrug design. Tam can be directly conjugated to conventional drugs and guiding drugs to estrogen receptor over-expressed cells. In addition, there is no limitation for the active ingredients used here in the present invention. The preferable active ingredients are compounds, nucleic acids, proteins, peptides, deoxyribonucleotides, ribonucleotides, oligonucleotides, imaging agents, fluorescent dyes or the combination thereof. The preferable moiety capable of binding estrogen receptor is compound of formula (II):

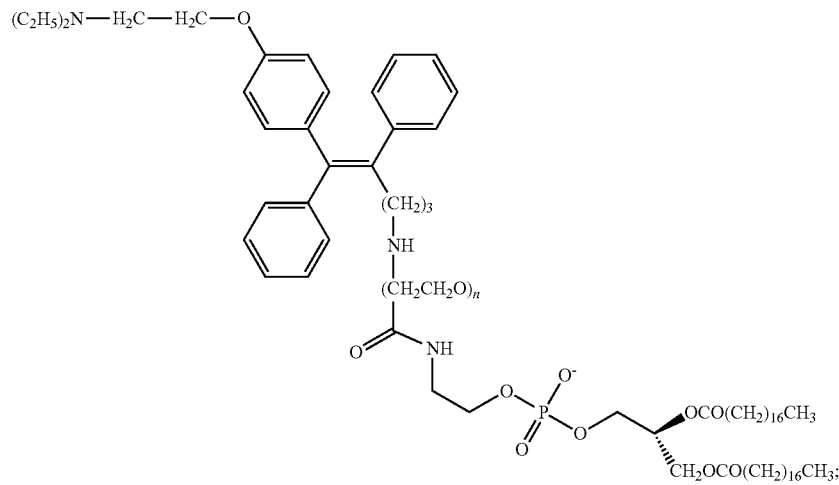

wherein n is an integer bigger than 5.

EXAMPLE 1

Synthesis of Tam Derivative (Tam-PEG-DSPE)

Figure 1:
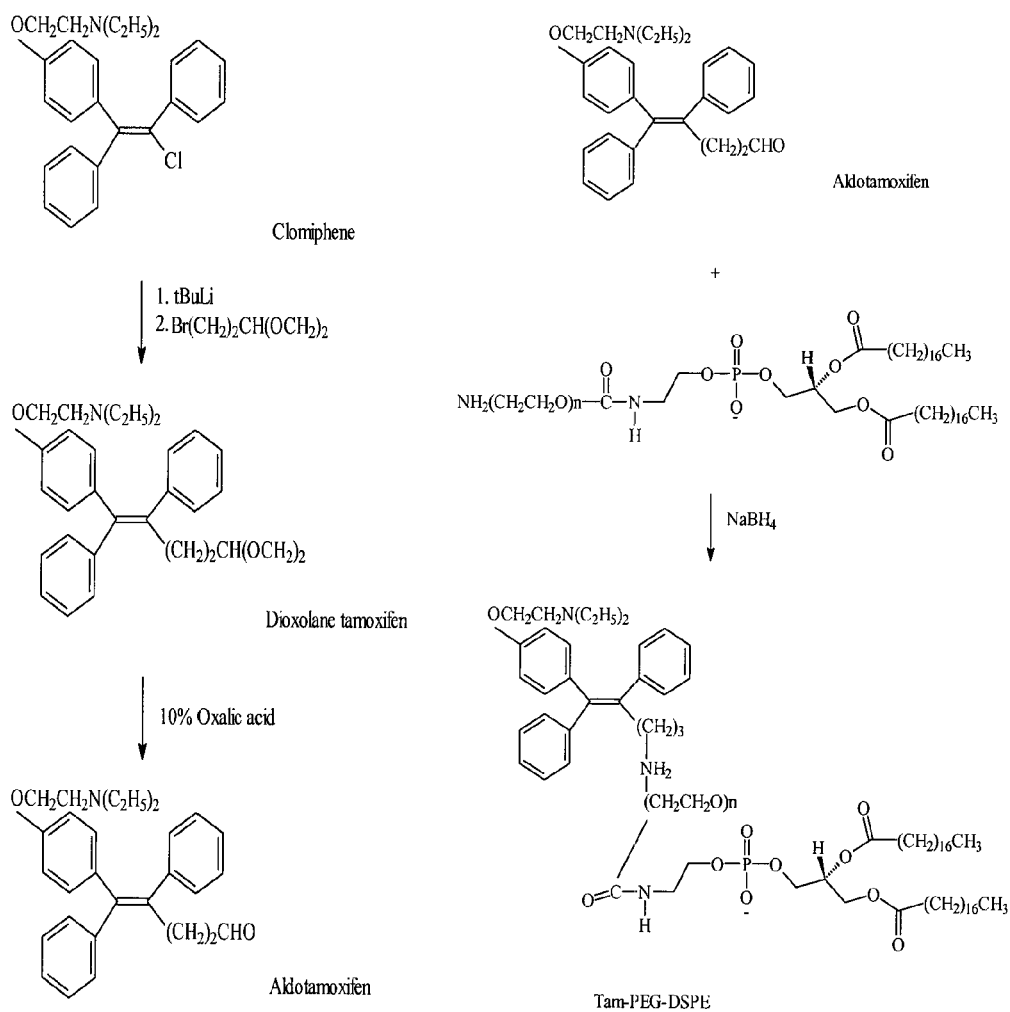
FIG. 1 is a synthetic scheme of the tam-PEG-DSPE of the present invention.

The synthetic scheme of Tam derivative is shown in FIG. 1. First, clomifene is reacted with tBuLi and 2-(2-bromoethyl) dioxolane to form dioxolane-tamoxifen. Then, dioxolane-amoxifen is oxidized with 10% oxalic acid to form aldotamoxifen. The synthesized aldotamoxifen is reacted with DSPE-PEG-amine in the presence of $NaBH_4$ to form a product Tam-PEG-DSPE of formula (II):

EXAMPLE 2

Preparation of Fluorescent Dye (DiI) Containing Liposomes

Liposomes are prepared by thin film hydration method. The formula of the liposomes is indicated in Table 1. Briefly, lipids (20 mg) mixtures are dissolved in ethanol and evaporated to dryness under a stream of nitrogen gas. Then the lipid film is hydrated with 10% sucrose solution at 60° C. followed by sonication for particle size reduction. The particle sizes are determined by laser particle analyzer, and the properties of the liposomes prepared here are shown in Table 1.

(II)

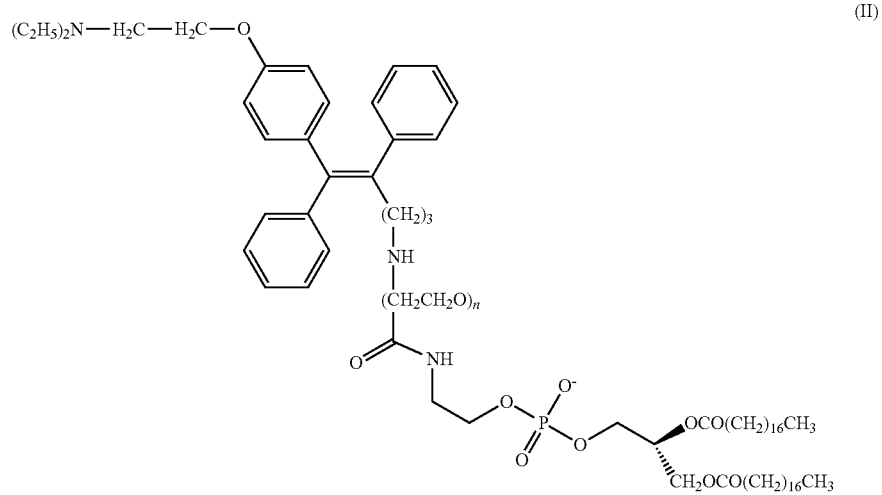

TABLE 1

Liposome formulation

| Formulation | Liposome composition (mole %) | | | | | Particle size (nm) |
|---|---|---|---|---|---|---|
| | PC | CHOL | DiI | PEG | Tam-PEG-DS PE | |
| Control liposome | 58 | 39.5 | 0.5 | 2 | — | 129.5 +/− 42.9 |
| Tam-liposome | 58 | 39.5 | 0.5 | — | 2 | 132.9 +/− 55.8 |

Liposome concentration = 20 mM

EXAMPLE 3

Cellular Uptake Study of DiI Containing Liposome-I

MCF-7 (receptor positive breast cancer cells) and ZR-75-1 (receptor positive breast cancer cells) cells are seeded in 8-well chamber slides with $5 \times 10^4$ cells per well 16 hr before further experiments hereafter. After overnight incubation, cells are respectively treated with various concentrations of DiI containing control liposomesor Tam-liposomes for 2 hours at 37° C., and then washed with PBS for three times. Subsequently, cells are fixed with 4% paraformaldehyde in PBS for 15 minutes at 4° C. Finally, cells are washed with PBS several times and are observed with the fluorescent microscopy. As a result, the fluorescence intensity of cells treated with Tam-liposomes is significantly stronger than that of the cells treated with control liposomes. It indicates that Tam-liposomes could enter those two ER over-expressed cells much more efficiently.

EXAMPLE 4

Cellular Uptake Study of DiI Containing Liposome-II

Figure 2:
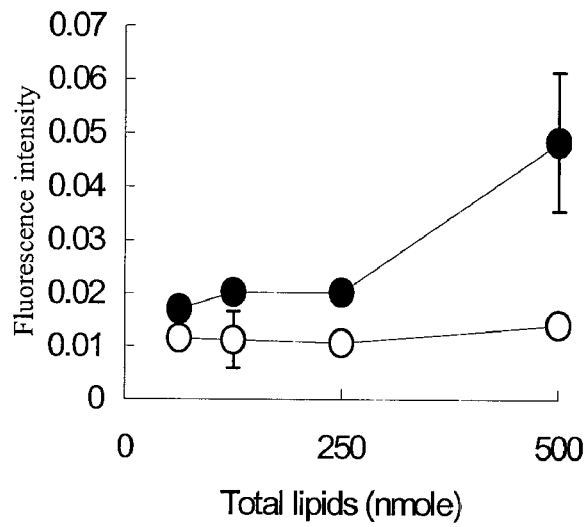
FIG. 2 is the fluorescence intensity of MCF-7 (2A) and ZR-75-1 (2B) cells after treatment with fluorescent dye containing control liposomes (○) or Tam-liposomes (●) for 4 hours at 37° C. in the embodiment 4 of the present invention.

MCF-7 and ZR-75-1 cells are seeded in 24-well plates with $5 \times 10^4$ cells per well 16 hr before further experiment here. After overnight incubation, cells are respectively treated with various concentrations of DiI containing control liposomes or Tam-liposomes for 4 hours at 37° C., and then washed with ice-cold PBS for one time. Subsequently, cells are incubated with 1% Triton X-100 surfactant in PBS for 1 hour at 37° C. for cell lysis. The cell lysates are taken out and the fluorescence intensity of these samples are analyzed with a fluorescence spectrometer. The result is shown in FIG. 2. The curves in FIG. 2 show that the delivery efficiency of Tam-liposomes is 3-5 times higher than that of control liposomes for those two ER over-expressed cells.

EXAMPLE 5

Free Ligand Competition Test

Figure 3:
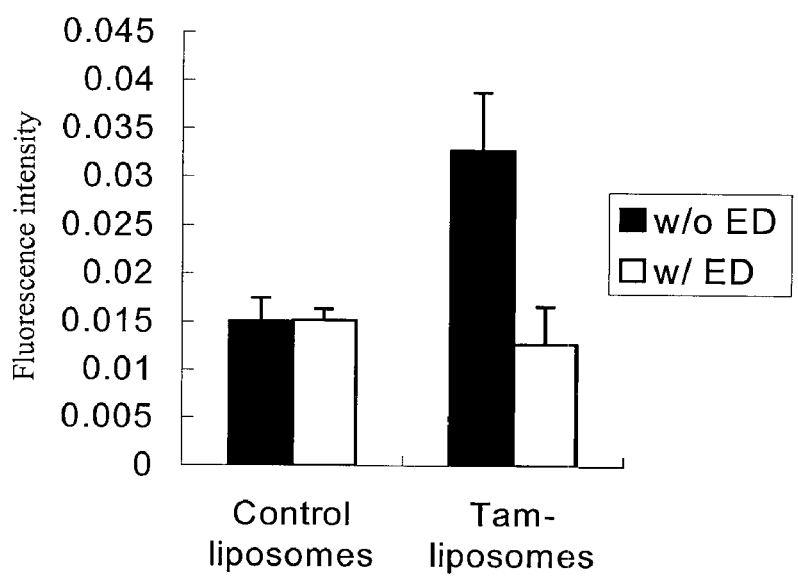
FIG. 3 is the fluorescence intensity of MCF-7 cells after treatment with control or Tam liposome in the presence or absence of free estradiol (ED) for 4 hours at 37° C. in the embodiment 5 of the present invention.

MCF-7 cells are seeded in 24-well plates with $5 \times 10^4$ cells per well 16 hr before the experiment. The experiment is performed after overnight incubation. Two hours before further treatment here, medium of the competitive group is replaced with medium containing 100 μM estradiol (ED). Two hours later, cells are respectively treated with DiI containing control liposomes or Tam-liposomes in a concentration of 500 nmole of total lipids for 4 hours at 37° C. in the presence or absence of 100 μM estradiol (ED), and then washed with ice-cooled PBS for one time. Subsequently, the cells are incubated with 1% Triton X-100 surfactant in PBS for 1 hour at 37° C. for cell lysis. The cell lysates are taken out and the fluorescence intensity of these samples are measured by a fluorescence spectrometer. The result is shown in FIG. 3. In the absence of ED, the delivery efficiency of Tam-liposomes is 2 times higher than that of control liposomes for ER over-expressed cells. However, in the presence of ED, there is no difference in delivery efficiency between Tam-liposomes and control liposomes. There is no difference between the delivery efficiencies of control liposomes in the presence or absence of ED. As a result, tamoxifen is capable of targeting to ER, guiding the liposomes to ER over-expressed cells, and thus increasing the delivery efficiency.

EXAMPLE 6

Preparation of Nanoparticle (NP)

Liposomes are prepared by thin film hydration method. Tam-liposomes are prepared according to the ratio: DSPG/DOPE/Tam-PEG-DSPE=49/49/2 (mole ratio). Control liposomes are prepared according to the ratio: DSPG/DOPE/DSPE-PEG=49/49/2 (mole ratio). NP can be obtained by mixing equal volume of the following solutions: FITC labeled oligonucleotide (F-ODN) and calf thymus DNA solution (0.1 mg/ml), 1.1 mg/ml charged peptide or polymer (such as polylysine, protamine) solution, and 0.3 mg/ml liposome suspension. Then the NP solution is kept at room temperature for 10 minutes before use. The particle size of NP is ranging between 150 to 200 nm, and the encapsulation efficiency for ODN is 100%.

EXAMPLE 7

Cellular Uptake Study of F-ODN Containing NP-I

MCF-7 cells are seeded in 8-well chamber slides with $2 \times 10^4$ cells per well 16 hr before further experiment here. After overnight incubation, cells are treated with F-ODN containing control NP or Tam-NP for 4 hours at 37° C., and then washed with PBS for three times. Subsequently, cells are fixed with MeOH for 1 minute and observed under a fluorescence microscope. As a result, the fluorescence intensity of cells treated with Tam-NP is significantly higher than that of the cells treated with control NP. It is indicated that Tam-NP could deliver more ODN into ER over-expressed cells.

EXAMPLE 8

Cellular Uptake Study of F-ODN Containing NP-II

Figure 4:
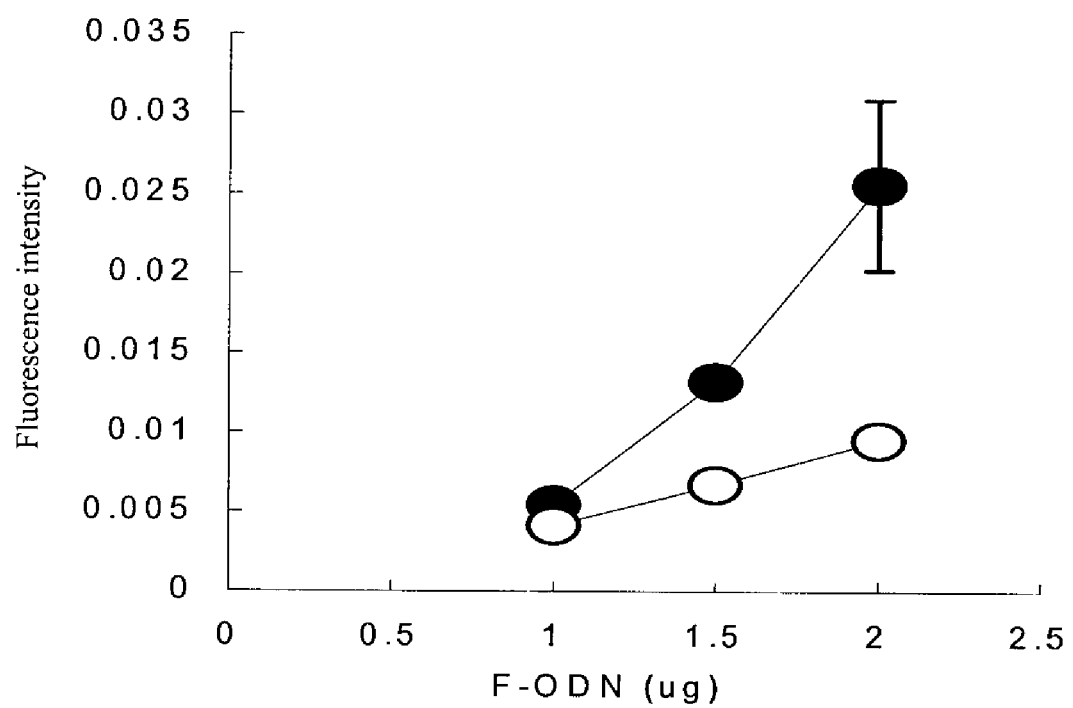
FIG. 4 is the fluorescence intensity of MCF-7 (4A) and HUVEC (4B) cells treated with FITC-ODN containing control nanoparticles (○) or Tam-nanoparticles (●) for 4 hours at 37° C. in the embodiment 8 of the present invention.

MCF-7 and HUVEC (human umbilical vein epithelia cell; receptor positive cells) cells are seeded in 24-well plates with $5 \times 10^4$ cells per well 16 hr before the experiment hereafter. After overnight incubation, cells are treated with various concentrations of F-ODN containing control NP or Tam-NP for 4 hours at 37° C., and then washed with ice-cold PBS for one time. Subsequently, the cells are incubated with 1% Triton X-100 surfactant in PBS for 1 hour at 37° C. for cell lysis. The cell lysates are taken out and the fluorescence intensities are analyzed with a fluorescence spectrometer. The result is shown in FIG. 4. The curves in FIG. 4 indicate that the delivery efficiency of Tam-NP is 2 times higher than that of control NP for ER over-expressed cells.

EXAMPLE 9

Targeted Effect of Tam Ligand

Figure 5:
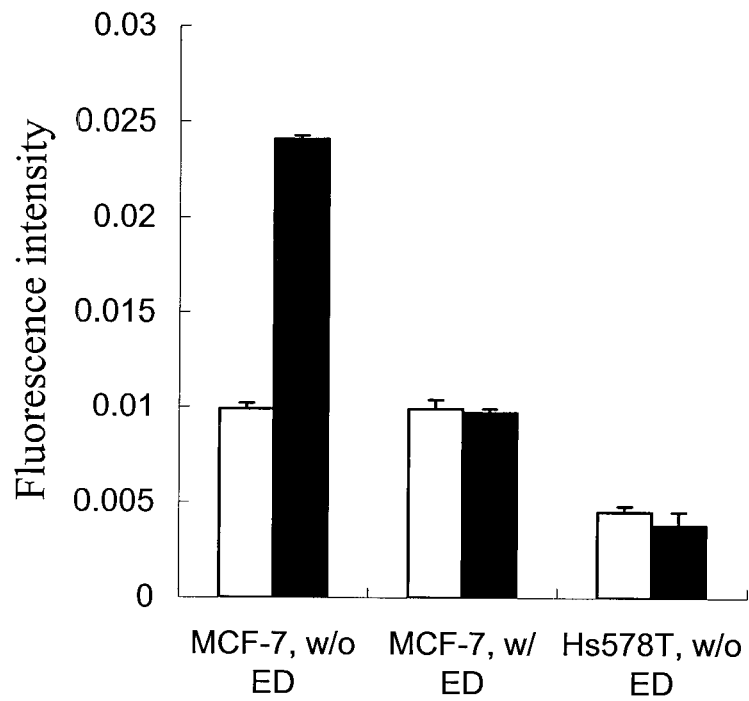
FIG. 5 is the fluorescence intensity of MCF-7 and Hs 578T cells after treatment with control nanoparticles (white column) or Tam-nanoparticles (black column) NP in the presence or absence of free estradiol (ED) for 4 hours at 37° C. in the embodiment 9 of the present invention.

MCF-7 and Hs 578T (human breast cancer cell line; receptor negative cells) cells are seeded in 24-well plates with $5 \times 10^4$ cells per well 16 hr before the experiment hereafter. The experiment is performed after overnight incubation. Two hours before treatment, medium of the competitive group is replaced 100 μM estradiol (ED) containing medium. Two hours later, cells are respectively treated with F-ODN containing control NP and Tam-NP for 4 hours at 37° C. in the presence or absence of 100 μM ED, and then washed with ice-cold PBS for one time. Subsequently, the cells are incubated with 1% Triton X-100 surfactant in PBS for 1 hour at 37° C. for cell lysis. The cell lysates are taken out and the fluorescence intensity of these samples are analyzed with a fluorescence spectrometer. The result is shown in FIG. 5. In the absence of ED, the delivery efficiency of Tam-NP is 2 times higher than that of control NP for ER over-expressed cells. However, in the presence of ED, the delivery efficiency of Tam-NP is inhibited to the same level as control NP. There is no difference between the delivery efficiencies of control NP and Tam-NP for the ER negative cells. As a result, tamoxifen is capable of specifically targeting to ER, guiding the NP to ER over-expressed cells, and thus increasing the delivery efficiency.

EMBODIMENT 10

Efficacy of Ex Vivo Experiment

Figure 6:
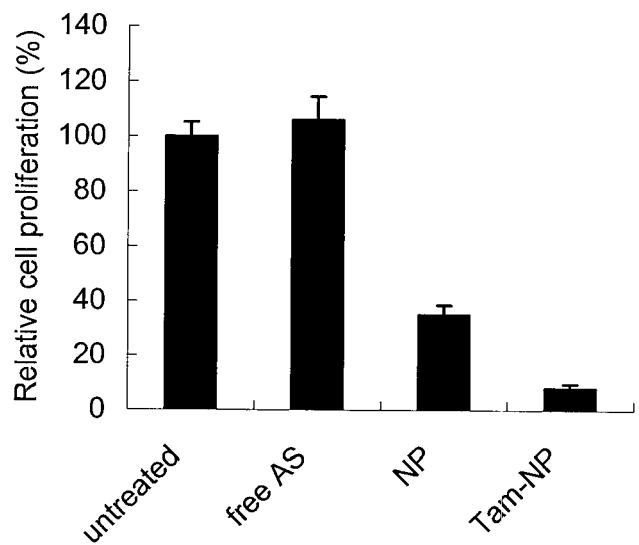
FIG. 6 is the growth inhibition effects of various formulas on MCF-7 cells in the embodiment 10 of the present invention.

Similar to the method mentioned above, potential antisense oligonucleotide (AS-ODN) are formulated into NP for the ex vivo experiment. The AS-ODN applied here is ISIS G3139 (against Bcl-2). MCF-7 cells are seeded in 24-well plates with $5 \times 10^4$ cells in each well 16 hr before further performing of the experiment here. After overnight incubation, cells are respectively treated with free AS-ODN, AS-ODN containing NP or Tam-NP for 4 hours at 37° C. The media are replaced with fresh media followed by incubation for another 72 hours. Then the survival cells are counted by trypan blue exclusion method. The result is shown in FIG. 6. According to the blocks shown in FIG. 6, Tam-NP could inhibit 90% of cell growth. NP alone inhibits 65% of cell growth. No inhibitory effect of free AS-ODN is observed. It indicates that Tam-NP could deliver more AS-ODN into ER over-expressed cells and exert stronger killing effect.

According to the embodiment illustrated above, the nanoparticles of the present invention certainly are capable of targeting the estrogen receptor over-expressed cells. Moreover, the nanoparticles of the present invention which containing active ingredients can efficiently enter the cells through estrogen receptor-mediated endocytosis.

Although the present invention has been explained in relation to its preferred embodiment, it is to be understood that many other possible modifications and variations can be made without departing from the spirit and scope of the invention as hereinafter claimed.

What is claimed is:

1. A drug delivery system for targeting estrogen receptor over-expressing cells, comprising:
   a plurality of nanoparticles, wherein said nanoparticles consist of one or more of the compounds selected from the group consisting of: lipids, surfactants, charged peptides, proteins, and polymers;
   active ingredients, wherein said active ingredients are encapsulated inside said nanoparticles or wherein said active ingredients form a complex with said nanoparticles; and
   a plurality of targeting ligands having a structure of the formula (I):

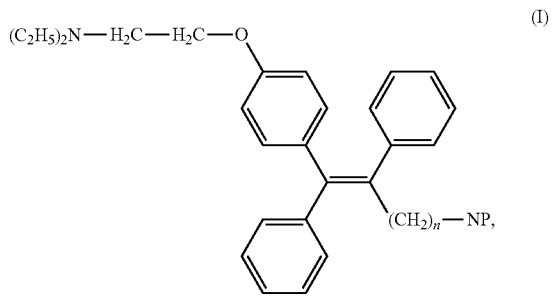

wherein n is an integer less than 10 and NP represents said nanoparticles, and
wherein said plurality of targeting ligands binds to estrogen receptor, and upon binding to estrogen receptor delivers the active ingredient to the estrogen receptor over-expressing cells.

2. The drug delivery system of claim 1, wherein at least one of said nanoparticles is a liposome, a polymer based nanosphere, an emulsion or a combination thereof.

3. The drug delivery system of claim 1, wherein said active ingredients are small molecular drugs, compounds, nucleic acids, proteins, peptides, DNA, RNA, oligonucleotides, imaging agents, fluorescent dyes or the combination thereof.

4. The drug delivery system according to claim 3, wherein said active ingredient is a nucleic acid.

5. The drug delivery system according to claim 3, wherein said active ingredient is ISIS G3139.

* * * * *